(12) United States Patent
Gandemo

(10) Patent No.: US 6,695,945 B2
(45) Date of Patent: Feb. 24, 2004

(54) METHOD OF ANCHORING FASTENING TABS TO SIDE PORTIONS OF A DISPOSABLE SANITARY GARMENT AND A DISPOSABLE SANITARY GARMENT COMPRISING FASTENING TABS ANCHORED BY SAID METHOD

(75) Inventor: Tomas Gandemo, Askim (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/975,068

(22) Filed: Oct. 12, 2001

(65) Prior Publication Data

US 2002/0045871 A1 Apr. 18, 2002

Related U.S. Application Data

(60) Provisional application No. 60/239,904, filed on Oct. 13, 2000.

(51) Int. Cl.[7] .................................................. B32B 31/00
(52) U.S. Cl. .................... 156/265; 156/66; 156/73.1; 156/270; 156/299; 156/300; 156/301; 156/302; 156/514; 156/519
(58) Field of Search .............................. 156/265, 302, 156/299, 514, 519, 518, 264, 66, 73.1, 270, 300, 301, 517, 520

(56) References Cited

U.S. PATENT DOCUMENTS

| 4,364,787 A | * 12/1982 | Radzins ..................... 156/164 |
| 4,382,303 A | * 5/1983 | Lunt ............................. 2/114 |
| 5,482,588 A | 1/1996 | Goulait et al. .............. 156/264 |

FOREIGN PATENT DOCUMENTS

WO    WO 00/01339    1/2000

* cited by examiner

*Primary Examiner*—Linda Gray
(74) *Attorney, Agent, or Firm*—Young & Thompson

(57) ABSTRACT

A method of anchoring fastening tabs to side portions of a disposable sanitary garment, such as a diaper or an incontinence guard includes the steps of cutting out holes in a backing sheet in opposite side portions of the rear or front part thereof; joining a top sheet to the cut backing sheet with an absorbent body disposed between these sheets to create a composite blank; placing fastening tabs in the side portions of the composite blank containing the cut out holes in the backing sheet with the manufacturer's ends of the tabs each being disposed in one of the holes, the tabs being made of a material which is compatible to the top sheet material from a welding point of view; and anchoring the manufacturer's ends of the fastening tabs to the top sheet by welding.

9 Claims, 2 Drawing Sheets

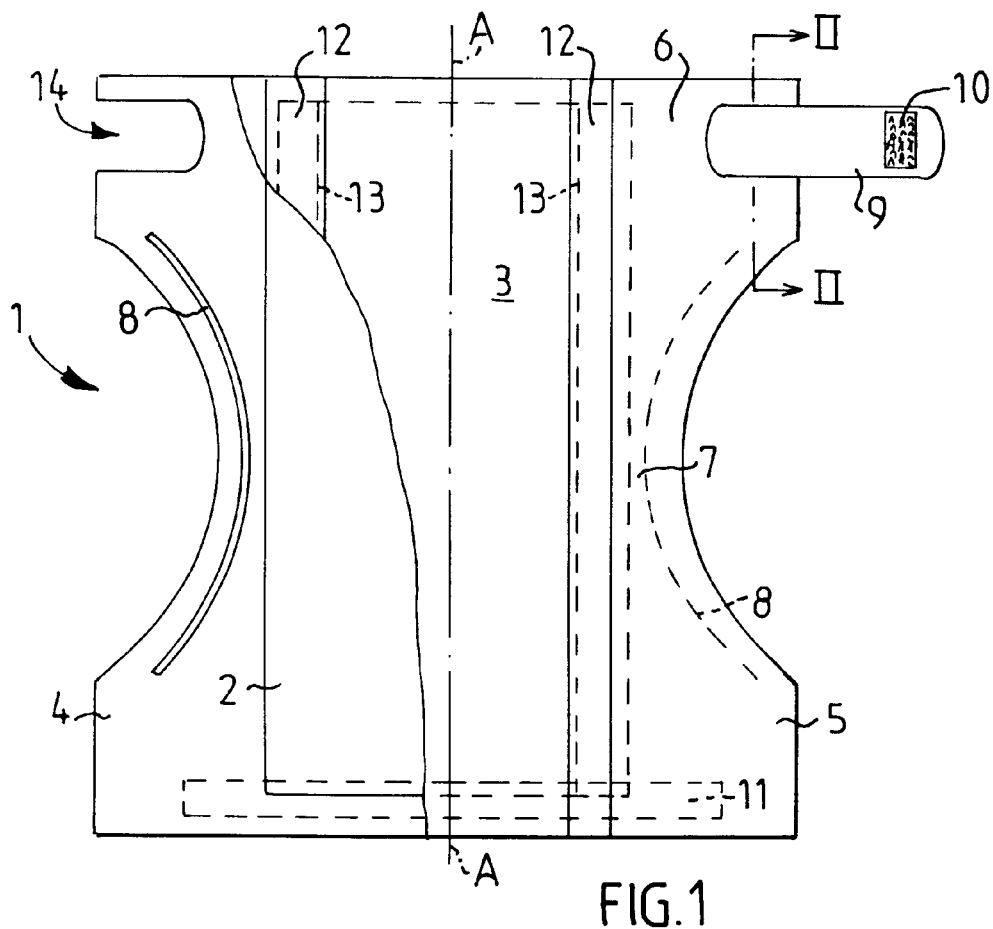
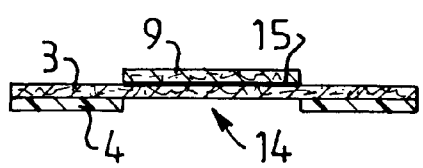
FIG. 2
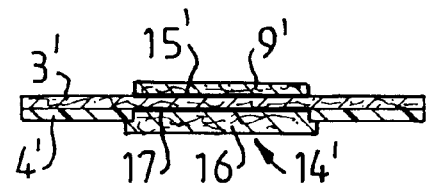
FIG. 3

METHOD OF ANCHORING FASTENING TABS TO SIDE PORTIONS OF A DISPOSABLE SANITARY GARMENT AND A DISPOSABLE SANITARY GARMENT COMPRISING FASTENING TABS ANCHORED BY SAID METHOD

This application claims benefit of provisional application No. 60/239,904, filed Oct. 13, 2000.

TECHNICAL FIELD

The present invention relates to a method of anchoring fastening tabs to side portions of a disposable sanitary garment, such as a diaper or an incontinence guard, said garment comprising a top sheet of liquid permeable, weldable material, a backing sheet of liquid impermeable material and an absorbent body enclosed therebetween, the top sheet and the backing sheet being extended outside the absorbent body around the periphery thereof and joined to each other in regions thereof lying outside the absorbent body, said garment having a front part, a rear part and an intermediate crotch part, wherewith laterally extending fastening tabs are fastened to the side portions in the rear or front part of the garment. The invention also relates to a disposable sanitary garment comprising fastening tabs anchored thereto by said method.

BACKGROUND OF THE INVENTION

In order to make the fastening tabs of disposable sanitary garments, such as diapers and incontinence guards, softer to the touch it is desirable to use non-woven material for such tabs. The risk for chafing is reduced if fastening tabs of materials softer than the materials commonly used for such tabs, e.g. polyethylene film, is used. It is also desirable to anchor the manufacturer's end of such tabs by weld joints instead of glue joints. The manufacturer's end of a fastening tab is the end thereof that is permanently fastened to a side portions of the garment by the manufacturer in contrast to the opposite end of the tab which is attached to a side portion of the garment by the user when applying the garment on a wearer. A weld joint can be made stronger than a glue joint and it exists for several reasons a general desire of reducing to a minimum the use of glue joints in manufacturing lines for absorbent garments. However, since the materials used for the backing sheet and the top sheet usually are incompatible with each other from a welding point of view, i.e. have different melting points, it is a problem to weld fastening tabs of soft non-woven material onto the side portions of the garment due to the incompatibility of the tab material and the backing sheet material.

The object of the invention is to provide a disposable sanitary garment, such as a diaper or an incontinence guard, with fastening tabs of soft material, the manufacturer's ends of the tabs being anchored to the side portions of the garment by a weld joint.

SUMMARY OF THE INVENTION

These object are accomplished by a method of anchoring fastening tabs to side portions of a disposable sanitary garment, such as a diaper or an incontinence guard, said garment comprising a top sheet of liquid permeable, weldable material, a backing sheet of liquid impermeable material and an absorbent body enclosed therebetween, the top sheet and the backing sheet being extended outside the absorbent body around the periphery thereof and joined to each other in regions thereof lying outside the absorbent body, said garment having a front part, a rear part and an intermediate crotch part, wherewith laterally extending fastening tabs are fastened to the side portions in the rear or front part of the garment, characterised by the following steps;

cutting out holes in a backing sheet in opposite side portions of the rear or front part thereof, between these sheets, thereby creating a composite blank, joining a top sheet to the cut backing sheet with an absorbent body disposed placing fastening tabs in the side portions of the composite blank containing the cut out holes in the backing sheet with the manufacturer's ends of said tabs each being disposed in one of said holes, said tabs being made of a material which is compatible to the top sheet material from a welding point of view, and anchoring the manufacturer's ends of the fastening tabs to the top sheet by welding.

In a preferred embodiment the cutting step consist of cutting successive rows of holes in a web of backing material which is continuously running in a machine direction.

In a first alternative the method includes the steps of laying a row of absorbent bodies on to the web of backing material, laying a web of top sheet material on the web of backing material, the web of top sheet material having the same width as the web of backing sheet material, joining the two webs together, thereby creating a continuous web of garment blanks, and thereafter welding fastening tabs to the side portions of the rear or front part of each garment blank.

In a second alternative the method includes the steps of laying a row of absorbent bodies on a continuously running web of top sheet material, the web of top sheet material having the same width as the web of backing sheet material, laying the web of backing material onto the web of top sheet material, joining the two webs together, thereby creating a continuous web of garment blanks, and thereafter welding fastening tabs to the side portions of the rear or front part of each garment blank.

In both alternatives the method preferably includes the steps of reinforcing the top sheet material in areas to which fastening tabs are anchored or are to be anchored, and anchoring the manufacturer's ends of the fastening tabs by ultra-sound welding The invention is also related to a disposable sanitary garment, such as a diaper or an incontinence guard, comprising a top sheet of liquid permeable, weldable material, a backing sheet of liquid impermeable material and an absorbent body enclosed therebetween, the top sheet and the backing sheet being extended outside the absorbent body around the periphery thereof and joined to each other in regions thereof lying outside the absorbent body, said garment having a front part, a rear part and an intermediate crotch part, wherewith fastening tabs are fastened to the side portions in the rear or front part of the garment, characterised in that the fastening tabs are made of a material which is compatible to the top sheet material from a welding point of view and that the backing sheet comprises cut-outs in the regions of the garment containing the manufacturer's ends of the fastening tabs such that no backing sheet material is present in those regions, and that the manufacturer's ends of the fastening tabs are fastened to the top sheet by weld joins.

In a preferred embodiment a strip of reinforcing material is attached to the top sheet in each region of the garment containing the manufacturer's end of a fastening tab. The top sheet consists of a non-woven material and the fastening tabs are made of a material containing the same type of fibres as the top sheet. Preferably, the top sheet and the fastening tabs are made of non-woven material containing polypropylene fibres and the manufacturer's end of the fastening tabs and the cut-outs in the backing sheet have a rounded shape, i.e. have no sharp corners. Furthermore, the backing sheet is extended a distance of 10–30 mm from the longitudinal side edge of each side portion in the rear or front part of the garment.

BRIEF DESCRIPTION OF THE DRAWING

The invention will now be described with reference to the enclosed drawing, in which;

FIG. 1 schematically shows a partially sectioned plan view of a diaper according to a preferred embodiment of the invention, FIG. 2 shows a cross-sectional view along line II—II of cross-section in FIG. 1, FIG. 3 shows a similar view as FIG. 2 of a diaper according to a second embodiment of the invention.

DESCRIPTION OF EMBODIMENTS

Figure 4:
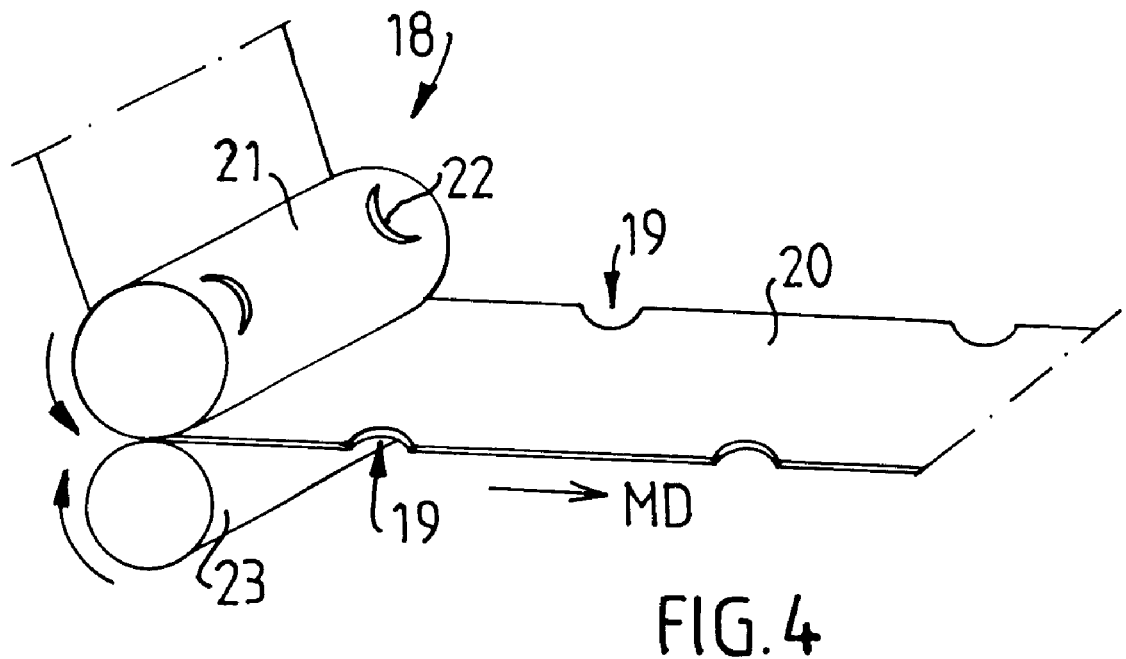
FIG. 4 illustrates schematically a device for performing a first cutting step in the method according to the invention.

In FIGS. 1 and 2 a disposable diaper 1 is disclosed. As is conventional in this field of the art, the diaper comprises an absorbent body 2, being enclosed between a liquid-permeable top sheet 3 and a liquid-impermeable backing sheet 4, these sheets being fastened to each other in portions thereof reaching beyond the absorbent body. The diaper has a front part 5, a rear part 6 and an intermediate crotch part 7, the longitudinal direction of the diaper extends from the rear to the front edge thereof. The diaper also comprises leg elastics 8, for example one or several elastic threads or bands disposed between the top sheet and the backing sheet along the sides of the diaper, at least in the crotch part thereof, and attached to the top sheet and/or backing sheet in a stretched state. In FIG. 1 all elastic components are shown in a stretched state.

The diaper 1 also comprises fastening tabs 9 projecting out from the lateral sides of the diaper in the rear part thereof. Only one of these fastening tabs is disclosed in FIG. 1. These fastening tabs have each a manufacturer's end which is permanently affixed to the respective side portion in the rear part of the diaper by the manufacturer of the diaper, and a user's end which is attached to a respective side portion in the front part of the diaper when the diaper is applied to a wearer by the person applying the diaper. The fastening tabs are provided with fastening elements 10, which in the disclosed embodiment consist of male fastener elements of a hooks and loops-type of fastener. The male elements 10 are engageable with female elements disposed on a band 11 attached to backing sheet on the outside thereof, i.e. the side of the backing sheet that is distal to the wearer during use of the diaper. Preferably, the male fastening elements are distanced from the respective end of the tabs in order to provide grip portions for the user of the diaper.

Furthermore, barrier flaps 12 are provided on the top sheet and are attached thereto along their distal edges, i.e. the edges distal from the longitudinal symmetry line A—A of the diaper. Along the proximal edges of flaps 12 elastic threads 13 are attached thereto in a stretched state.

The fastening elements 10 are in the shown embodiment male fastener elements in fasteners of the hooks and loops type. Other types of mechanical fasteners can of course also be used, such as snap fasteners, buttons and holes and the like. It is also conceivable to use adhesive fasteners.

The liquid-permeable top sheet 3 is made of a soft skin-friendly material. Examples of suitable materials are different types of non-woven. Other material that can be used are perforated plastic films, plastic nets or knittted, crotcheted or woven textile materials or combinations and laminates of the above mentioned types of material. The plastic material can be a thermoplastic material, for example polypropylene (PP). The non-woven material can be formed of synthetic fibres, such as PE, polypropylene (PP), polyurethane (PU), a polyester, nylon or regenerated cellulose, or a mix of different fibres. All materials used for top sheets in absorbent sanitary garments and containing weldable fibres can be used for the top sheet 3 and the above mentioned materials are only given as examples. The top sheet can also comprise different materials in central and side parts thereof. The parts of the top sheet 3 lying laterally outside the barrier flaps 12 can be made of a liquid impermeable material whereas the central part between the flaps 12 is made of a liquid permeable material.

The liquid-impermeable backing sheet 4 consists of a flexible material, preferably a thin plastic film of PE, PP or a polyester but could also consist of a laminate of a liquid-permeable material, such as a non-woven, and a liquid-impermeable material. All materials that are used for liquid-impermeable backing sheets are conceivable. The backing sheet can advantageously be air-permeable.

The absorbent body 2 is preferably formed of cellulose fibres but also other natural materials, such as cotton fibres or peat can be used. Alternatively can absorbent synthetic fibres or a mixture of natural and synthetic fibres be used. The absorbent body can also comprise a super-absorbent, i.e. a polymer having the capacity to absorb liquid to an amount several times larger than its own weight. The absorbent body can also contain form stabilising and/or liquid dispersing components and also bonding agents for holding together short fibres and particles to a continuous unit. Furthermore, the absorbent body can contain more than one layer of absorbent material.

The fastening tabs 9 are made of one or several layers of non-woven material. Thereby a soft fastening tab is obtained which greatly reduces the risk of chafing against the skin of a wearer that exist for tabs made of harder material, such as a plastic film. Moreover, the fastening tabs 9 are attached to the top sheet 3 by weld joins. Such joins are desirable since they can be made stronger than glue joins. The fastening tabs 9 could advantageously be elastic in order to improve the comfort to the wearer in the waist area and to cope with the difference in waist size that appear when a wearer change from a sitting to a lying position. Such tabs are preferably made of two non-woven layers, between which strips of elastic material or several elastic threads have been attached in a stretched state, at least in the areas thereof between the manufacturer's and the user's ends. Examples of elastic bands that can be used are given in EP-A-494 941. Alternatively, the fibres in the non-woven material used for the fastening tabs could be elastic or be a mixture of elastic and non-elastic fibres.

It is often the case that the backing sheet material is not compatible with the top sheet material from a welding point of view, i.e. these materials have different melting points. This incompatibility leads to a problem when a fastening tab should be fastened to the composite layer of backing sheet material and top sheet material by thermal welding, such as ultra sonic welding. This problem is solved in the present invention by providing cut-outs or holes 14 in the side portions of the backing sheet in the rear or front part of the diaper to which the fastening tabs 9 should be attached. Thereby, the material in the fastening tabs 9 need only be compatible from a welding point of view with the top sheet material and can consequently be chosen without consideration of the material that the backing sheet is made of. As is evident from the cross-sectional view in FIG. 2, the weld join 15 is made in an area free of backing sheet material.

The cut-outs or holes 14 are preferably extending 10–30 mm from each longitudinal edge of the side portion of the rear part of the diaper 1 laterally towards each other, but can also as a whole be distanced from the longitudinal edges of the side portion of the rear part of the diaper 1 as long as the holes have a size equal to or larger than the manufacturer's end of the fastening tab. Preferably, the cut-outs and the manufacturer's ends of the tabs 9 have a rounded shape with no sharp corners in order to further reduce the risk for chafing. The total extension of the cut-outs in the lateral direction of the diaper could be up to half the maximum width of the diaper, but lies preferably between 20–40 mm. The extension of the cut-outs in the longitudinal direction of the diaper is smaller than the length of the longitudinal edge of the side portion containing the cut-out.

FIG. 3 shows a similar view as FIG. 2 of a diaper according to a second embodiment of the invention. This diaper is in most aspects similar to the diaper 1 shown in FIGS. 1 and 2 and the description of the embodiment according to these Figures is generally valid also for the diaper according to FIG. 3. Therefore, components in FIG. 3 corresponding to identical components of FIGS. 1 and 2 are given the same reference numerals with the addition of a prime sign. The only difference between the embodiments is that a reinforcing strip of material 16 is affixed to the top sheet 3' by a weld join 17 in the areas defined by cut-outs 14'. The strip of material 16 is made of a material compatible with the top sheet material from a welding point of view, preferably from a material comprising the same type of fibres as the top sheet. By the use of reinforcing strips it is possible to reduce the thickness of the top sheet material and thereby reduce the material costs for the diaper.

The step of cutting cut-outs or holes in the backing sheet is easy to incorporate in a conventional line for continuous manufacturing of disposable diapers. In such a line, a first continuous web of backing sheet material or top sheet material is successively running through a device for coating the web with glue, a device for laying a row of absorbent bodies onto the web, a device for laying leg elastics on the web, a device laying a second web of top sheet material or backing sheet material onto the composite web consisting of the first web, the row of absorbent bodies and the leg elastics, a device for affixing fasteners, and a cutting device for making leg cut-outs and for cutting individual diapers out of the composite web. In FIG. 4 is schematically shown a cutting device 18 for cutting two rows of holes 19 in the sides of a web 20 continuously running in a machine direction MD. The device 18 comprises a cutting roller 21 provided with knives 22 and an anvil roller 23, the web 20 passing between these rollers. If the first web is a web of backing sheet material, the device 18 is placed in the manufacturing line upstreams of the glue coating device and if the first web is a web of top sheet material, the cutting device 18 is placed outside the transport line for the first web and upstreams of the device for delivery of the second web onto the first web. The cutting of the web of backing sheet material can also be done in a separate line comprising a device for winding the cut web of backing sheet material onto a storage roller which in turn is used in a conventional line for manufacturing of diapers. In a manufacturing line according to the present invention the composite web passes an ultra sonic welding device for welding fastening elements onto the top sheet.

Figure 5:
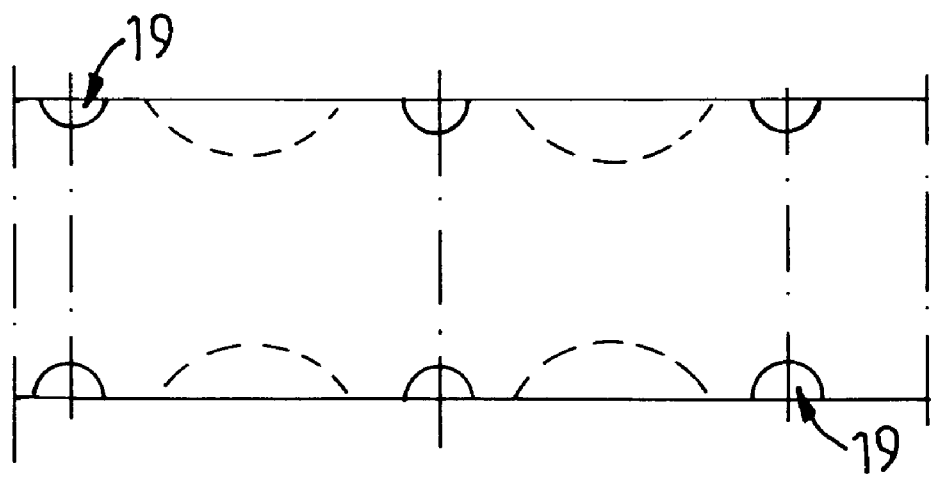
FIG. 5 illustrates schematically a continuous web of backing sheet blanks.

In FIG. 5 a plan view of web according to FIG. 4 is shown. By interrupted lines is shown how the backing sheet is cut in the final stage of an alternative manufacturing line. As is evident from this Figure, the holes 19 have an extension also in the front part of the individual diapers cut out by this alternative way of manufacturing.

The embodiment described can of course be modified in several respects without leaving the scope of invention. For example, the holes or cut-outs in the side portions of the rear part of the disposable sanitary garment can have other shapes than disclosed. Other types of barrier flaps could be used and the end parts of such flaps can be used as reinforcing material instead of strip of material 16. Moreover, the side portions of the top sheet can be provided with reinforcement material in the whole area thereof. The fastenings tabs can be provided on the side of the top sheet being distal from the wearer instead of on the side being proximal thereto as in the shown embodiments. The absorbent body can have other shapes than the shown rectangular shape, for example an hour-glass shape. Furthermore, the fastenings tabs and thereby the cut-outs in the backing sheet could be disposed in the side portions of the front part of the garment instead of in the rear part as in the embodiments shown, even if this is not preferred. The diaper can also be provided with waist elastics of conventional type substituting or complementing elastic fastening tabs. The invention can also be used on other types of disposable sanitary garments, such as incontinence guards. The scope of invention shall therefore be determined only by the content of the enclosed patent claims.

What is claimed is:

1. A method of anchoring fastening tabs to side portions of a disposable sanitary garment, said garment comprising a top sheet of liquid permeable, weldable material, a backing sheet of liquid impermeable material and an absorbent body enclosed therebetween, the top sheet and the backing sheet being extended outside the absorbent body around the periphery thereof and joined to each other in regions thereof lying outside the absorbent body, said garment having a front part, a rear part and an intermediate crotch part wherewith laterally extending fastening tabs are fastened to the side portions in the rear or front part of the garment, characterised by the following steps;

cutting out holes in a backing sheet in opposite side portions of the rear or front part thereof, joining a top sheet to the cut backing sheet with an absorbent body disposed between these sheets, thereby creating a composite blank, placing fastening tabs in the side portions of the composite blank containing the cut out holes in the backing sheet with the manufacturer's ends of said tabs each being disposed above one of said holes, said tabs being made of a material which is compatible to the top sheet material from a welding point of view, and anchoring the manufacturer's ends of the fastening tabs to the top sheet by welding.

2. The method according to claim 1, characterised by cutting successive rows of holes in a web of backing material which is continuously running in a machine direction.

3. The method according to claim 2, characterised by laying a row of absorbent bodies on to the web of backing material, laying a web of to sheet material on the web of backing material, the web of top sheet material having the same width as the web of backing sheet material, joining the two webs together, thereby creating a continuous web of garment blanks, and thereafter welding fastening tabs to the side portions of the rear or front part of each garment blank.

4. The method according to claim 2, characterised by laying a row of absorbent bodies on a continuously running web of top sheet material, the web of top sheet material having the same width as the web of backing material, laying the web of backing material onto the web of top sheet material, joining the two webs together, thereby creating a continuous web of garment blanks, and thereafter welding fastening tabs to the side portions of the rear or front part of each garment blank.

5. The method according to claim 1, characterised by reinforcing the top sheet material in areas to which fastening tabs are anchored or are to be anchored.

6. The method according to claim 1, characterised by anchoring the manufacturer's ends of the fastening tabs by ultra-sound welding.

7. The method according to claim 4, characterised by reinforcing the top sheet material in areas to which fastening tabs are anchored or are to be anchored.

8. The method according to claim 4, characterised by anchoring the manufacturer's ends of the fastening tabs by ultra-sound welding.

9. The method according to claim 5, characterised by anchoring the manufacturer's ends of the fastening tabs by ultra-sound welding.

* * * * *